(12) United States Patent
Martel et al.

(10) Patent No.: US 8,948,841 B2
(45) Date of Patent: Feb. 3, 2015

(54) MR-TRACKING BASED ON MAGNETIC SIGNATURE SELECTIVE EXCITATION

(75) Inventors: Sylvain Martel, Quebec (CA);
Jean-Baptiste Mathieu, Montreal (CA);
Ouajdi Felfoul, Saint-Laurent (CA);
Gilles Beaudoin, Saint-Lambert (CA)

(73) Assignees: Polyvalor, Limited Partnership, Montreal (CA); Val-Chum, Limited Partnership, Montreal (CA)

( * ) Notice: Subject to any disclaimer, the term of this patent is extended or adjusted under 35 U.S.C. 154(b) by 1199 days.

(21) Appl. No.: 11/993,320

(22) PCT Filed: Jun. 22, 2006

(86) PCT No.: PCT/CA2006/001045
§ 371 (c)(1),
(2), (4) Date: Dec. 22, 2009

(87) PCT Pub. No.: WO2006/136029
PCT Pub. Date: Dec. 28, 2006

(65) Prior Publication Data
US 2010/0168553 A1  Jul. 1, 2010

Related U.S. Application Data

(60) Provisional application No. 60/693,082, filed on Jun. 23, 2005.

(51) Int. Cl.
*A61B 5/055* (2006.01)
*A61B 19/00* (2006.01)
*G01R 33/28* (2006.01)

(52) U.S. Cl.
CPC ............. *A61B 5/055* (2013.01); *A61B 19/52* (2013.01); *A61B 19/5244* (2013.01); *G01R 33/286* (2013.01); *G01R 33/287* (2013.01); *A61B 2019/5236* (2013.01)
USPC ............ 600/411; 600/424; 324/307; 324/309

(58) Field of Classification Search
USPC .......... 600/410–411, 420, 423, 424; 324/307, 324/309
See application file for complete search history.

(56) References Cited

U.S. PATENT DOCUMENTS

| 6,476,607 | B1 | 11/2002 | Dannels et al. |
| 7,962,194 | B2 * | 6/2011 | Martel et al. ................. 600/411 |
| 2004/0210128 | A1 | 10/2004 | Martel et al. |

(Continued)

FOREIGN PATENT DOCUMENTS

EP   1 300 675   4/2003

OTHER PUBLICATIONS

Kochavi et al., "Method for Rapid MRI Needle Tracking," Magnetic Resonance in Medicine, Wiley-Liss, Inc., 2004, pp. 1083-1087.

(Continued)

*Primary Examiner* — Ruth S Smith
(74) *Attorney, Agent, or Firm* — J-Tek Law PLLC; Jeffrey D. Tekanic; Scott T. Wakeman

(57) ABSTRACT

The present invention relates to a MR tracking method and device. More specifically, the present invention relates to a magnetic resonance tracking method and device, using a magnetic-susceptible object. A magnetic iso-surface induced by the object is selectively excited with a corresponding frequency offset; the magnetic iso-surface is then projected on three axes of a k-space, from which projections the spatial position of the object is calculated.

11 Claims, 15 Drawing Sheets

(56) References Cited

U.S. PATENT DOCUMENTS

| | | |
|---|---|---|
| 2005/0018949 A1 | 1/2005 | Yan |
| 2005/0054913 A1 | 3/2005 | Duerk et al. |
| 2005/0054914 A1 | 3/2005 | Duerk et al. |
| 2005/0261575 A1 | 11/2005 | Conolly et al. |

OTHER PUBLICATIONS

Haacke et al., "Magnetic Resonance Imaging: Physical Principals and Sequence Design," Wiley-Liss, 1999, pp. 118.

Wacker et al., "The Catheter-Driven MRI Scanner: A New Approach to Intravascular Catheter Tracking and Imaging-Parameter Adjustment for Interventional MRI", AJR 2004;183:391-395.

Mathieu et al., "Preliminary Studies for Using Magnetic Resonance Imaging Systems as a Mean of Propulsion for Microrobots in Blood Vessels and Evaluation of Ferromagnetic Artefacts", IEEE CCECE (Canadian Conference on Electrical and Computer Engineering) 2003 Proceedings, Montréal, May 2003.

\* cited by examiner

FIG_1

FIG_2

(a) and (b) are MS-SET images of the magnetic object in two locations (c) And (d) MS-SET Projections obtained by acquiring one k-space line. The maximum of the correlation between (c) and (d) gives the distance in pixel between these two curves. The correlation is shown in (e)

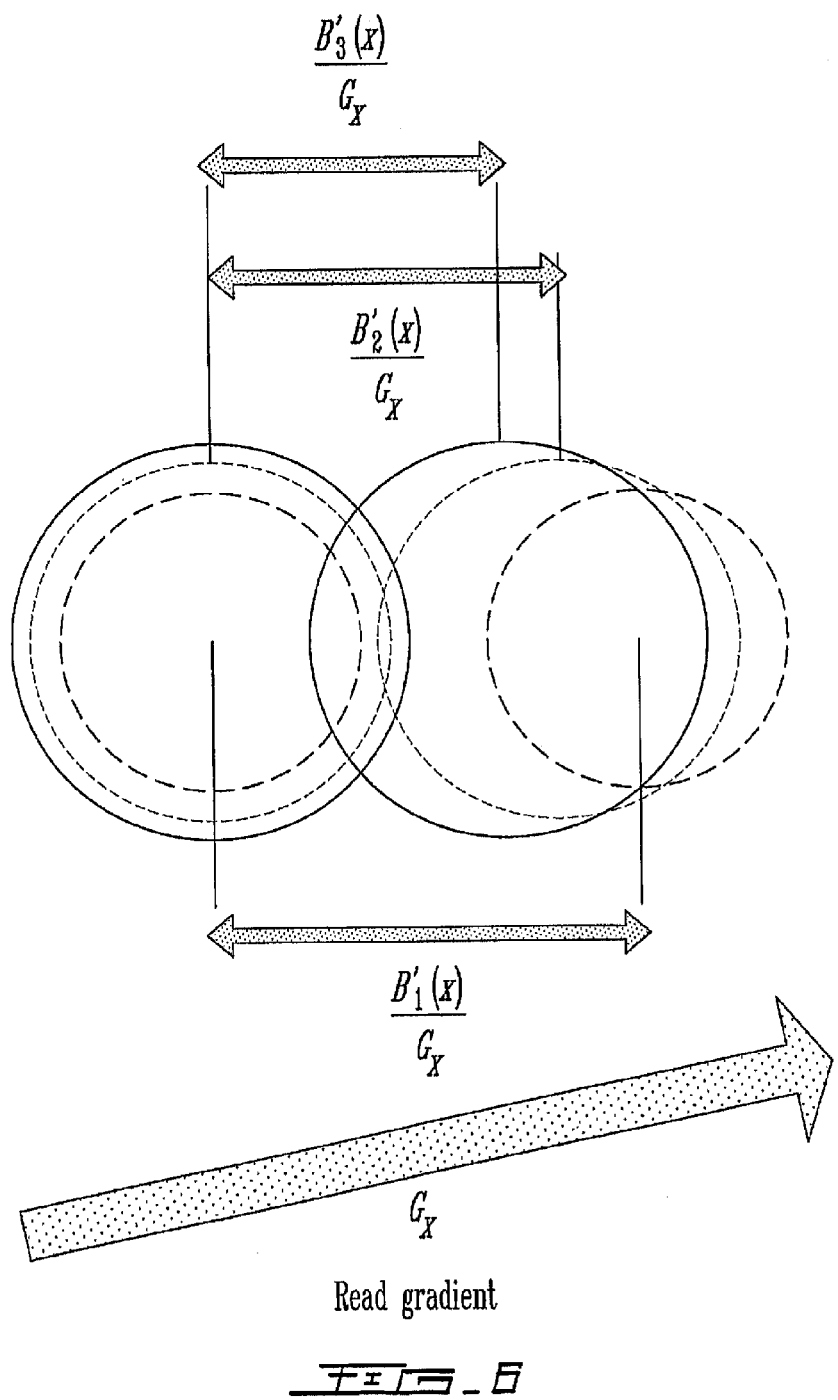
FIG_8

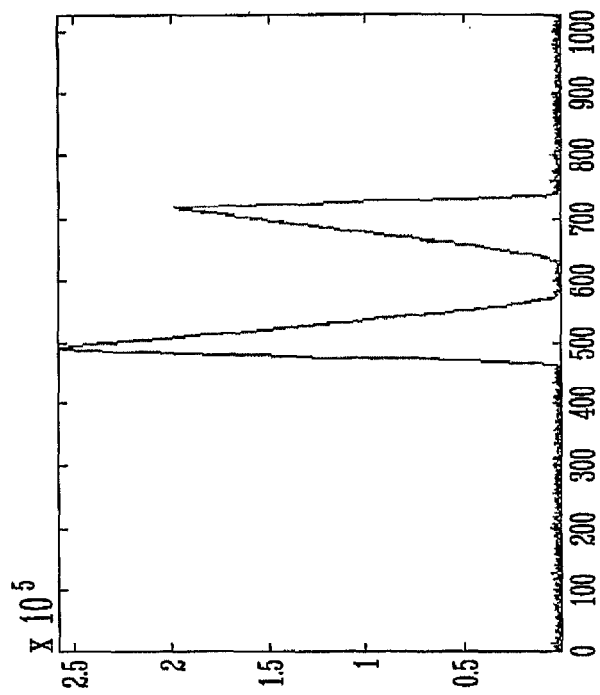
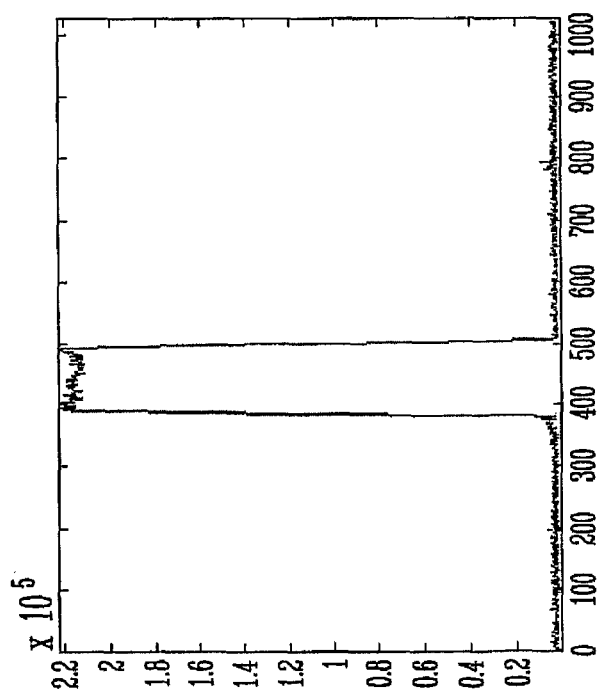

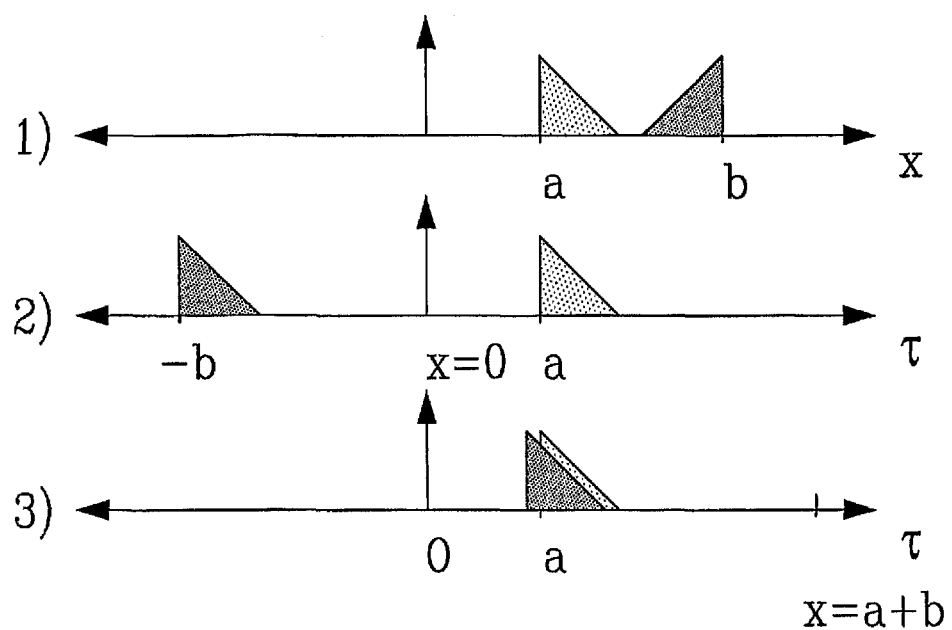
FIG_15

US 8,948,841 B2

MR-TRACKING BASED ON MAGNETIC SIGNATURE SELECTIVE EXCITATION

CROSS-REFERENCE

This application is the US national stage of International Patent Application No. PCT/CA2006/001045 filed on Jun. 22, 2006, which claims priority to US Provisional Patent Application No. 60/693,082 filed on Jun. 23, 2005.

FIELD OF THE INVENTION

The present invention generally relates to a tracking method and device for tracking tethered and untethered objects inside the human body.

BACKGROUND OF THE INVENTION

Consistent and reliable tracking of an inserted device is one of the critical requirements for the success of MR-guided (Magnetic Resonance) endovascular interventions and as such, several methods have been reported. These tracking methods may be categorized either as passive, semi-active, or active.

Passive tracking methods exploit the susceptibility difference between the tissue and the inserted device. These passive methods are typically simpler but slower compared to other methods.

Semi-active methods are similar to the passive methods except that the susceptibility difference necessary to cause a signal loss is controlled through external means. This is typically done through the induction of a magnetic field that modifies the MR-signal by activating a coil integrated as part of the inserted device.

The complexity of the inserted device increases substantially with an active method with the addition of an antenna to measure the induced NMR (Nuclear Magnetic Resonance) signals from the surrounding protons to determine the position through three axial projections. Active methods typically provide superior spatial and temporal resolutions. Unlike passive methods, substantial increases in temperature, problematic for human interventions have been recorded in both active and semi-active tracking methods mainly due to the induced current along the length of the conducting wires by the applied RF (Radio Frequency) waves.

Untethered microdevices under development contain a ferromagnetic core and are propelled by magnetic forces induced by the magnetic gradients generated with an MRI system (Magnetic Resonance Imaging). This method is referred to as MRP (Magnetic Resonance Propulsion). In this context, an MRI system is not only used to image the region of interest, but also to propel a ferromagnetic microdevice, determine its location, compute the corrective actions through feedback controls to adjust the generation of the magnetic gradients. These adjustments are necessary to navigate such a microdevice in a pre-planned path inside the blood vessels. As such, being unable to track such a device within specific real-time constraints would prevent the feasibility of such an interventional technique. The main motivation behind MRP is that an untethered implementation may be suitable in order to reduce the risks of encumbrance of the blood vessels and tissue damages in more complex pathways caused by the friction of existing tools such as a catheter or other tethered devices. These microdevices may eventually be useful for performing tasks in remote sites that are presently inaccessible or at high risks with existing tools. These tasks could include but are not limited to thermal treatment of tumors at selected sites, highly localized drug delivery for chemotherapy, on-site delivery of MRI contrast agents, and carriers for biosensing applications.

For human interventions, the overall diameters of such unthetered devices are generally constrained to ~10.5 mm when operating in the aorta, 1.0-4.0 mm in large arteries, and could theoretically have diameters down to ~0.006-0.010 mm when operating in capillaries. These values depend on several factors including but not limited to blood flows, the diameter of the blood vessels, the size of the ferromagnetic core inside the device, the shape of the device, the corresponding drag force, the ferromagnetic material being used, and the amplitude and duty cycle of the applied magnetic gradients.

In known passive tracking methods, small paramagnetic rings are typically mounted as markers on catheters and guidewires. These markers produce local field distortions appearing as areas of signal loss in MR imaging in a region surrounding the markers. Furthermore, this positioning by signal loss, referred to as negative contrast, is limited to regions of high signal intensity where the signal loss can be detected without ambiguity. More recently, a novel approach to passive tracking of paramagnetic markers has been described where positive contrast of the markers to their background (white marker tracking) is exploited. With this method, a dephasing gradient is added in the direction of the slice selection during excitation to enhance the contrast between the markers and the background. This compensation gradient induces a signal loss in the image through dephasing and rephrasing of the signal surrounding the area of perturbed magnetic field, resulting in a positive contrast (instead of a negative contrast when no compensation gradient is used), the markers appearing bright on a darker background. A positive contrast can also be obtained with a bead or a coating with is doped with a 4-6% Gd-DTPA solution and applied to the instrument to generate an increase of the MR signal. The Gd-DTPA is characterized by reducing the longitudinal relaxation time of surrounding tissues and shows more signal than biological tissues when the images are acquired with a very short repetition time. The addition of a compensation gradient further improves the contrast between the instrument and the background. Unfortunately, these methods are still image-based methods. Although trade-offs may be achieved between spatial and temporal resolutions, these methods are far too slow in achieving an acceptable spatial resolution to be integrated within the real-time constraints of MRP-based applications.

Recently, a new method for rapid MRI tracking has been described in Kochavi E, Goldsher D, Azhari H. *Method for rapid MRI needle tracking.* Magn Reson Med 2004; 51:1083-1087, where six central k-space lines were usually sufficient to locate a needle at the cost of an increase in computation. However, this method does not deal with image artifacts and only applies within a given 2D image slice.

SUMMARY OF THE INVENTION

An object of the present invention is to provide an improved Magnetic resonance tracking based on magnetic signature selective excitation.

Another object of the present invention is to provide a tracking method and device requiring the acquisition of only three k-space lines along three linearly independent axes in order to locate an object in 3D, the three k-space lines defining three projections of the object.

Another object of the present invention is to provide a tracking method and device whose resolution, precision and required acquisition time overcome the disadvantages of previous passive MR-tracking methods where the necessary acquisition and processing time and the poor resolution prevent their use for clinical applications.

A further object of the present invention is to provide a tracking method and device which rely on a new sequence that is easy to use with clinical MRI system and thus may be customized depending on the application requirements.

According to an aspect of the present invention, there is provided a method for magnetic resonance tracking comprising:

provinding a magnetic-susceptible object;
selectively exciting an induced magnetic iso-surface about the object;
projecting the excited induced magnetic iso-surface on three axes G1, G2 and G3 in k-space to obtain three projection lines representing the position of the excited induced magnetic iso-surface on the three axes; and
calculating the position of the object from the three projections.

According to another aspect of the present invention, there is provided a device for magnetic resonance tracking comprising:

means for providing a magnetic-susceptible object;
means for selectively exciting an induced magnetic iso-surface about the object;
means for projecting the excited induced magnetic iso-surface on three axes G1, G2 and G3 in k-space to obtain three projection lines representing the position of the excited induced magnetic iso-surface on the three axes; and
means for calculating the position of the object from the three projections.

The foregoing and other objects, advantages and features of the present invention will become more apparent upon reading of the following non-restrictive description of illustrative embodiments thereof, given by way of example only with reference to the accompanying drawings.

BRIEF DESCRIPTION OF THE DRAWINGS

In the appended drawings:

FIG. 6 is a schematic view of the effect of background gradient on image encoding;

FIGS. 7a through 7d show transversal and sagittal MRI images, respectively in FIGS. 7a and 7b, of the dipole when excited with an RF frequency of 2 kHz for a duration of 2560 μs the coronal and sagittal images are similar; projection along the read axis of FIGS. 7a and 7b being shown respectively in FIGS. 7c and 7d;

FIG. 15 constitutes an intuitive representation of the convolution tracking method for real vectors

DETAILED DESCRIPTION OF THE ILLUSTRATIVE EMBODIMENTS

Generally stated, a tracking method and device according to a non-restrictive embodiment of the present invention will now be described. The tracking method and device have been developed within the constraints imposed by the use of untethered microdevices in medical interventions which follow pre-planned paths inside blood vessels. In this case, since a passive tracking method is preferable for simplicity and miniaturization purposes, an approach was developed to improve the spatial and temporal resolution. It should be understood that although the present invention is presented herein in the context of interventional MR-guided endovascular operations based on miniature untethered devices, it may also be used as a passive tracking method with other tools, for example tethered devices such as catheters, guidewires or needles.

The tracking method according to a non-restrictive, illustrative embodiment of the present invention is referred to as Magnetic Signature Selective Excitation Tracking (MS-SET) and is based on the selective excitation of magnetic iso-surfaces caused by an induced magnetic field from a magnetic-susceptible object to be tracked. To be magnetic-susceptible, the object preferably includes ferromagnetic, ferrimagnetic, paramagnetic, superparamagnetic and/or supramagnetic materials that can be shaped into a suitable trackable object or an agglomeration of magnetic micro or nano particles. Alternatively, coils installed on catheters, guidewires, needles or other medical instruments may be used as the magnetic-susceptible object to be tracked. Positive contrast images are obtained with reference to the position of the magnetic source. A correlation function performed on only one k-space line for each of the three linearly independent axes, corresponding to three projections, is used to obtain a 3D location of the object. In other words, only three linearaly independent axes G1, G2 and G3 are required to obtain the 3D localization of the object.

Figure 1:
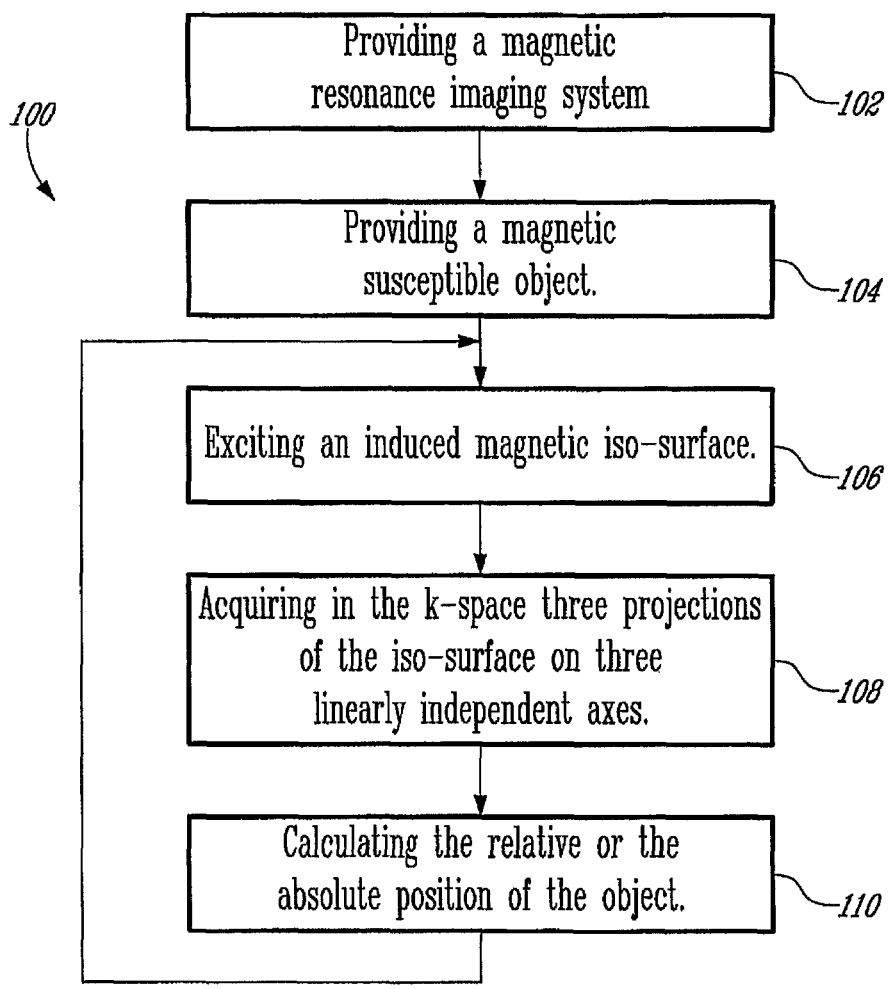
FIG. 1 is a block diagram of a method according to an illustrative embodiment of the present invention.

Turning now to FIG. 1 of the appended drawings, a method 100 according to an illustrative embodiment of the present invention will be described.

The first step 102 is providing an MRI system, which is used to acquire the data as well as perform the usual calculations in a k-space, as known by a person skilled in the art.

The second step 104 consists in providing a magnetic-susceptible object, which is an object that react to an external magnetic field or a variation thereof, whether or not it self-generates its own magnetic field in the absence of an external magnetic field. The object is to induce magnetic iso-surfaces that are each sensitive to a specific frequency.

Turning now to step 106, the MRI system is used to generate the adequate frequency for exciting a chosen iso-surface induced by the magnetic-susceptible object.

In step 108, three projections of the excited and induced magnetic iso-surface are acquired by the MRI system along three linearly independent axes.

Using these three projections, step 110 calculates a relative or a absolute position of the object. Of course, the position of the tracked object is advantaegously displayed for immediate use and/or stored for future use, The various steps of the method generally described hereinabove will now be discussed in greater details.

The induced magnetic field from a small object with an arbitrary shape can be approximated by the field of a dipole as described by Equation 1 where $\mu_0 = 4\pi 10^{-7}$ H·m$^{-1}$ is the permeability of free space.

$$\vec{B}'(P) = \frac{\mu_0}{4\pi}\left(3\frac{(\vec{m}\cdot\vec{r})\vec{r}}{r^5} - \frac{\vec{m}}{r^3}\right) \quad \text{Equation 1}$$

For a uniformly magnetized sphere, the dipolar magnetic moment $\vec{m}$(A·m$^2$) is given by:

$$\vec{m} = \frac{4}{3}\pi a^3 \vec{M}_{SAT} \quad \text{Equation 2}$$

where $\vec{M}_{SAT}$ is the saturation magnetization of the sphere, and a its radius (m).

Figure 2:
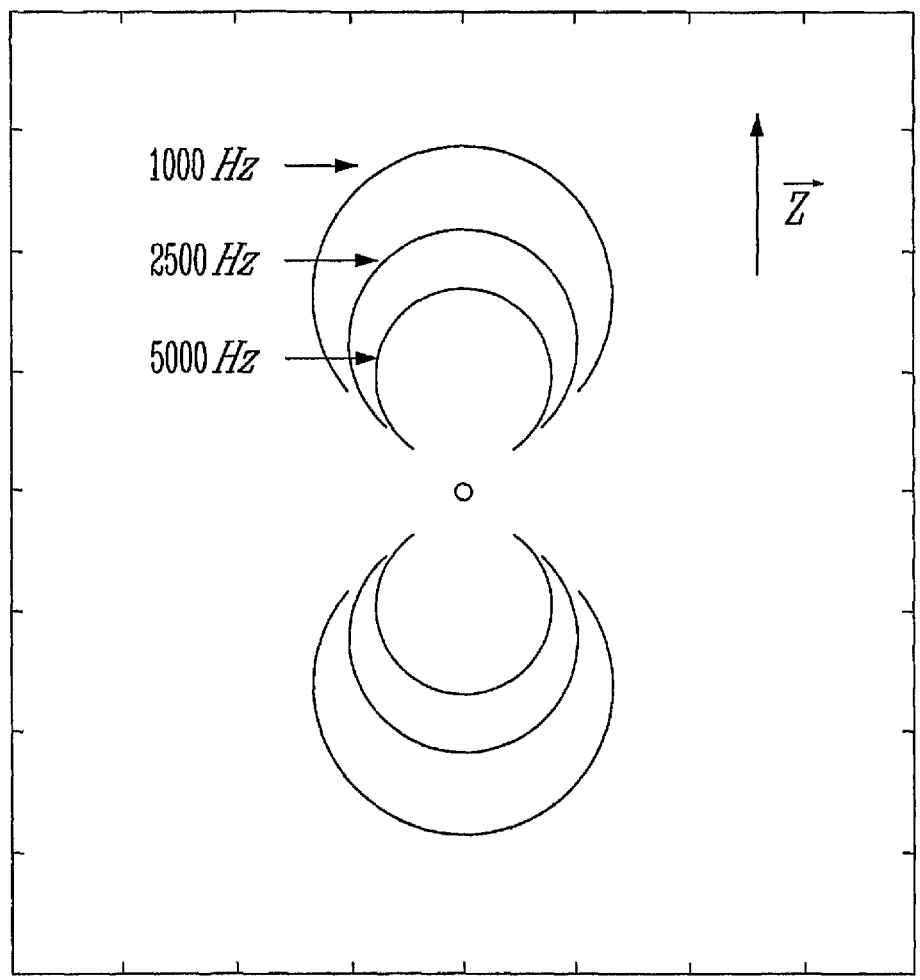
FIG. 2 shows spatial distributions of spins with the same resonant frequency of 1 kHz, 2.5 kHz, and 5 kHz.

The tracking method according to an illustrative embodiment of the present invention is generally based on the application of an RF excitation tuned to the frequency of the desired magnetic iso-surface as given in FIG. 2. FIG. 2 illustrates three magnetic iso-surfaces of the same object when submitted to RF excitation at three different frequencies. As can be seen from this figure, the iso-surface becomes closer to the object as the excitation frequency is increased.

Figure 3:
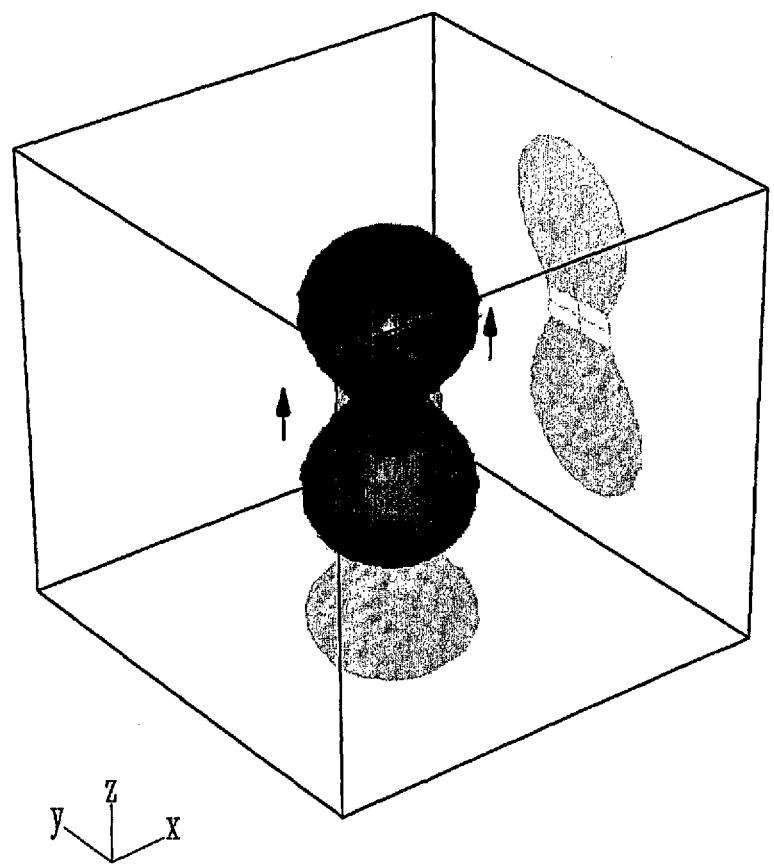
FIG. 3 is a 3D simulation of the excited volume and corresponding projection images with the method of the present invention.

Encoding the positions of the excited spins is done through the application of the readout gradient as it is the case with traditional MRI sequences. A projection image of the magnetic iso-surface, as depicted in FIG. 3, is therefore obtained. The shape of the magnetic iso-surface depends, amongst others, on the excitation frequency as well as in the object's magnetic signature. The projection of the given image along the read axis, corresponding to the central line of the k-space along the same axis, gives the 1D marker position. Unlike conventional passive tracking methods, MS-SET requires only three k-space lines for 3D tracking, resulting into a significant gain in speed.

Figure 4:
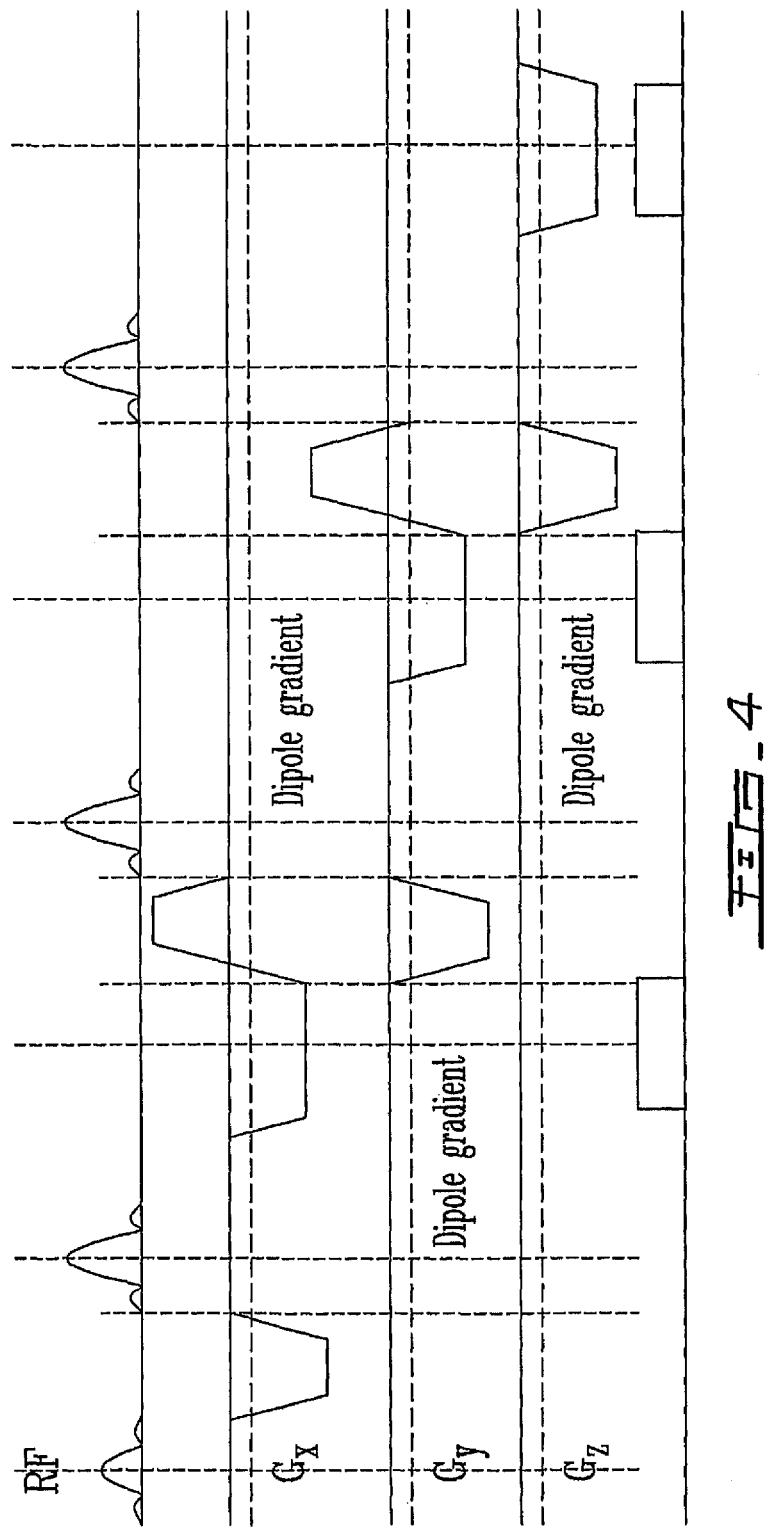
FIG. 4 shows a spin echo sequence used for imaging.

In the non-restrictive, illustrative embodiment of the present invention, the MS-SET tracking method employs a modified Spin Echo (SE) sequence where the slice select gradient is removed, as shown in FIG. 4. A SE rather than a gradient echo implementation was chosen due to its capacity to rephase the excited spins. The general Spin Echo sequence is described in E. Mark Haacke, Robert W. Brown, Michael R. Thompson, Ramesh Venkatesan, "Magnetic Resonance Imaging: Physical Principals and Sequence Design" WILEY-LISS, 1999, p 118.

In FIG. 4, an example of a Spin Echo sequence used for tracking is illustrated. There is no slice select gradient applied other than the dipole gradient (dashed lines) which is always present. The frequency of the RF excitation pulse is tuned to a given magnetic iso-surface. Three projections which may be orthogonal for simplicity purpose, are acquired with a single RF excitation.

As will easily be understood by one skilled in the art, a gradient echo implementation can also be used. However, the MR signal will be attenuated due to T2* effect. A z-dephaser gradient can be added in the direction parallel to the read axis in order to enhance the signal. As will easily be understood by one skilled in the art, the slice select gradient has been removed to allow the projection on the entire volume and not only on a single slice. The gradient is not required since its role is usually to spatially discriminate the zones that will be excited by the RF signal. This role is taken by the gradient induced by the object to be tracked. It is to be noted that the frequency offset and the duration of the RF excitation pulse to adjust the RF bandwidth may be changed through customized dialog boxes (not shown) available to the MRI operator.

The illustrative embodiment of the MS-SET method will be further explained with reference to the following non-restrictive example.

Experiments were done that aimed at characterizing the tracking method by quantifying its performance criteria in terms of accuracy and precision. To ensure highly reliable positions and displacements for characterization purposes, the ferromagnetic sphere was mounted on a specially made gauge structure that was fastened on top of a rectangular phantom (200×300 mm). The gauge structure made of garolite offered a positioning reference for the sphere as well as precise position increments of 10 mm±15 µm and 15 mm±15 µm along the MRI axes x and z respectively. This experimental set-up was previously calibrated and characterized using a Mitutoyo Legex 106 Coordinate Measuring Machine (CMM). A maximum assembly imprecision of ±25 µm resulting from differences between the nominal and actual sphere positions were recorded. This imprecision translates to 17% of the size of a pixel and as such, it should not affect reliability in the characterization of the tracking method.

The entire volume of the phantom was filled with 7 liters of water mixed with 20 g/l gelatin, 1.25 g/l nickel sulphate, and 5 g/l NaCl, providing a solid homogeneous medium with short relaxation times. The ferromagnetic core was made of a chrome steel sphere with a diameter of 1 mm. The saturation magnetization of this alloy is $\vec{M}_{SAT}=1.36\times10^6$ A/m. This value was measured with a vibrating sample magnetometer (Princeton Applied Research Corp. model 155). The magnetization of the ferromagnetic core reached saturation when placed in a 1.5 T bore of a Siemens Magnetom Avanto MRI system used for experimentation.

For each position, three projections were taken, one for each orthogonal axis. The first position, acquired when no increment was added, was considered as the reference. The measured displacement corresponded to the strongest correlation between each subsequent position and the first one.

Figure 9:
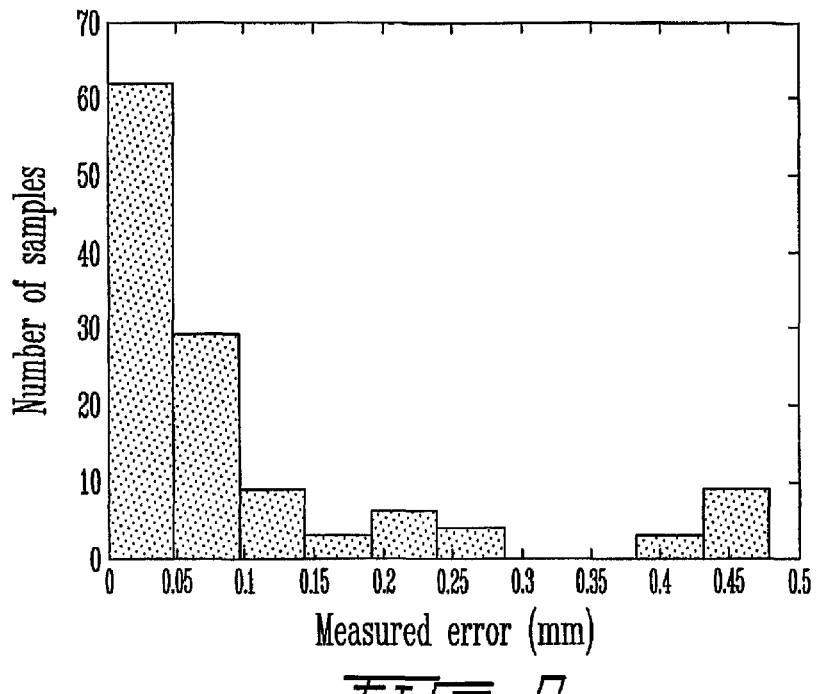
FIG. 9 is a histogram of errors obtained from several repetitions between the measured positions and the real positions.

The following results are presented in order to demonstrate the repeatability and accuracy of the above described MS-SET method. Table 1 gives the real and measured displacements as well as the average error for 5 different positions. For each position three projections were acquired along three orthogonal directions. In addition, each projection was repeated three times, which gives a total of 45 measurements. No noticeable variations are measured between the three repetitions, validating the repeatability criterion of the suggested technique. The data is assembled in a histogram, illustrated in FIG. 9, which shows the distribution of the magnitude of the error of the relative position for all measurements. A global average of 0.102 mm is obtained which could be further reduced to 0.065 by eliminating the 2nd measurement in x which is an outlier.

TABLE 1

Theoretical versus measured displacements and corresponding errors

| | Position | | | | |
|---|---|---|---|---|---|
| | 1 | 2 | 3 | 4 | 5 |
| Real displacement in z (mm) | 14.986 | 14.986 | 9.991 | 0 | 9.991 |
| Real displacement in x (mm) | 0 | 9.991 | 0 | 9.991 | 14.986 |
| Measured displacement in z (mm) | 14.958 | 14.938 | 10.068 | 0.011 | 9.920 |
| Measured displacement in x (mm) | 0.126 | 10.441 | 0.146 | 9.959 | 15.018 |
| Measured error in z (mm) | 0.038 | 0.049 | 0.077 | 0.0122 | 0.071 |
| Measured error in x (mm) | 0.126 | 0.450 | 0.146 | 0.034 | 0.032 |
| Global mean error (mm) | | | 0.102 | | |

Figure 5B:
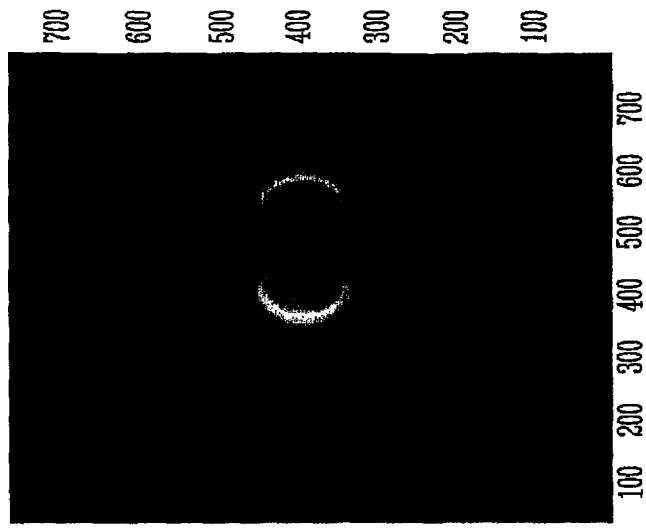
FIGS. 5a and 5b illustrate MS-SET images of the magnetic object in two locations.
Figure 5A:
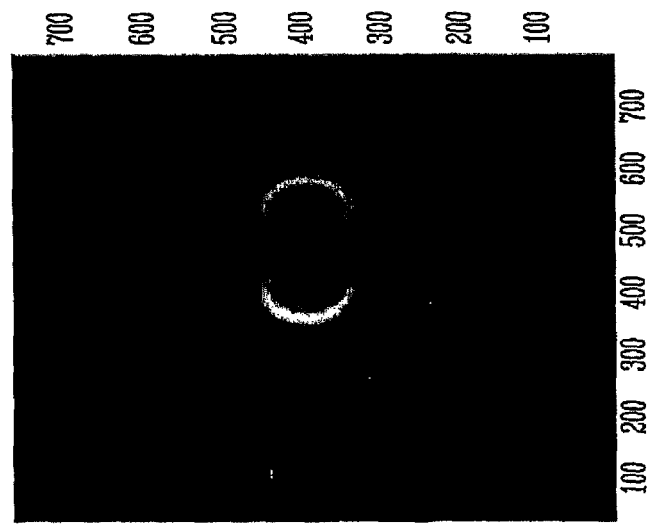
Figure 5D:
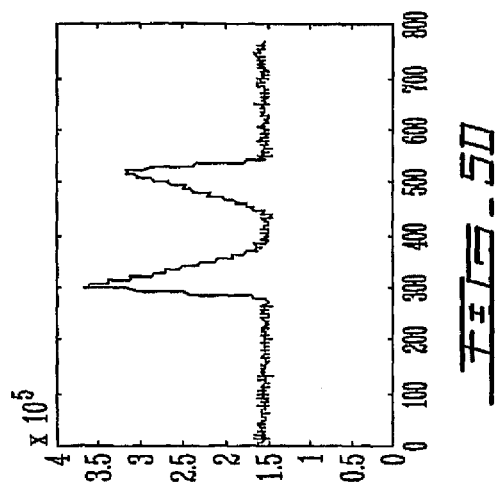
FIGS. 5c and 5d show MS-SET projections obtained by acquiring one k-space line.
Figure 5E:
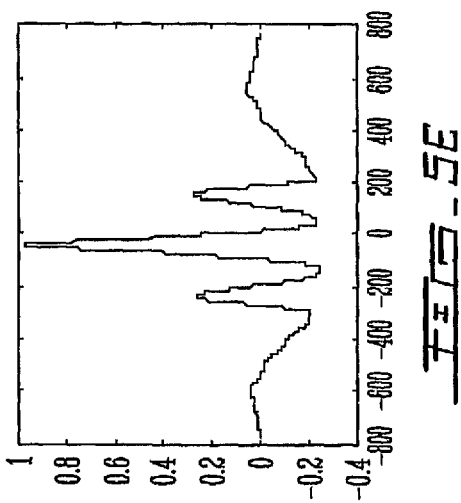
FIG. 5e shows the correlation between FIGS. 5c and 5d, with FIGS. 5a through 5e illustrating the determination of the displacement along one of the axes required to obtain an updated 3D position.
Figure 5C:
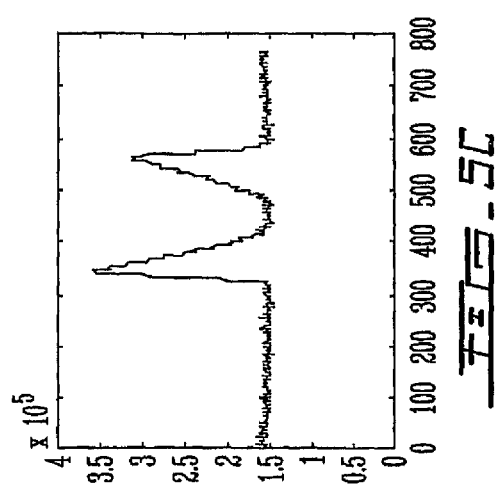

FIGS. 5a through 5e illustrate the determination of one of the axes required to obtain the final 3D position. In these figures, we suppose that the image 5a is an image of the initial position of the object, and projection 5c is the projection along the x axis from the acquisition of the central k-space line only. Image 5b corresponds to a subsequent position of the object with its projection shown in FIG. 5c. The correlation between the projection of FIG. 5d and the projection of FIG. 5c gives the distance between the two positions. It is to be noted that the images of FIGS. 5a and 5b are shown herein for illustration purposes. Indeed, no image is required in the present method that determines the position of the object solely using the projections as described herein.

The above discussion with reference to FIG. 5 gives only the relative position of the object. When an absolute position is required, for example, the position between the object and the center of the MRI, one must take into account the geometric distortions caused by the magnetic field generated by the object as will be discussed hereinbelow.

Referring back to FIG. 4, in the imaging process the dipole's magnetic field remains present during readout encoding and acts as additional gradients (dotted lines in the figure) that are superposed to the imaging gradients. This background field causes the location of spins to be shifted along the read axis as a function of the field strength. The perturbed encoded position is given by:

$$x' = x + \frac{B'}{G_x} \quad \text{Equation 3}$$

In Equation 3, x' is the resulting translated position along the axis of the readout gradient of the excited spins found at position x. B' is the value of the dipole's magnetic field given by the RF excitation pulse. $G_x$ is the readout gradient along the x-axis.

From Equation 3 and for a given offset excitation frequency, the effect of pixel shifting is reduced by increasing the applied readout gradient intensity. Table 2 presents an order of magnitude of the spatial translation errors that occurs for some readout gradient and frequency offset. Tracking the marker relatively to the reference axes of the MRI is possible if these encoding errors are compensated, which is complicated when considering a practical RF pulse tuned to excite a wide range of magnetic field values as showed in FIG. 6. Due to the $1/r^3$ dependence of the dipole's magnetic field, spins near the device experience a more pronounced shift than those further away.

It is to be noted that, in the present non-limitative example, geometric distortion was not considered. Instead, relative positioning was performed.

TABLE 2

Effects of the magnitude of the reading gradients and offset frequency on the encoding errors

| RF Excitation (Hz) | Read gradient amplitude (mT/m) | Displacement (mm) |
|---|---|---|
| | 1 | 23.5 |
| | 5 | 4.7 |
| 1000 | 10 | 2.3 |
| | 40 | 0.58 |
| | 1 | 35.2 |
| | 5 | 7 |
| 1500 | 10 | 3.5 |
| | 40 | 0.88 |
| | 1 | 47 |
| | 5 | 9.4 |
| 2000 | 10 | 4.7 |
| | 40 | 1.2 |

Absolute Positioning

By taking two readings of a position, one with positive readout gradients and one with negative readout gradients, it is possible to get the absolute position of the device. Because the distortion is inversely proportional to the readout gradient, the projection of the magnetic signature will be approximately reversed when the gradient is reversed. Convoluting the projections obtained with opposite gradients will give a maximum at a position related to the center of the device.

To illustrate this method intuitively, let's name $M_+(x)$ a projection mask with a magnetic element arbitrarily placed at $x_0$ acquired using a positive readout gradient $G_R$; and $M_-(x)$ a mask of the same element, at the same position $x_0$, taken with the same readout gradient magnitude but pointing in the opposite direction ($-G_R$). Suppose now that $M_+(x)$ is composed of a pattern $A(x-x_0)$. From the above discussion, we can deduce that $M_-(x)$ will be a reflection of the pattern A around $x_0$, that is $A(x_0-x)$. Convolving $M_+$ with $M^*_-$:

$$C(x) \equiv M_+(x) \otimes M^*_-(x) \quad (1)$$
$$= A(x-x_0) \otimes A^*(x_0-x)$$
$$= \int_{-\infty}^{\infty} A(x-x_0-\tau)A^*(x_0-\tau)d\tau$$

where the superscript * represents the complex conjugate. C(x) will have its global maximum when the two A patterns overlap, that is, for x=2*$x_0$. Knowing $x_0$, the absolute position of the bead with respect to the center of the MRI bore, it is then possible to use the relative positioning method to get absolute positions by using $M_+$ as the correlation mask.

FIG. 15 constitutes an intuitive representation of the convolution tracking method for real vectors where: 1) $M_+(x)$ and $M_-(x)$, arbitrary real signals displaying symmetry around the position $(a+b)/2$; 2) $M_-(x-\tau)$ and $M_+(\tau)$ with $x=0$; and 3) $M_-(x-\tau)$ and $M_+(\tau)$ with $x=a+b$.

Imaging

Figures 7A, 7B:

FIGS. 7a and 7b illustrate images based on a magnetic signature selective excitation. These images depicted in FIGS. 7a and 7b are high resolution (1024 ×1024) projection images in the axial and sagittal planes of an object, respectively. A frequency offset of 2 kHz was used which is exciting lobes at approximately 15 times the sphere diameter. FIGS. 7c and 7d show the projection along the read axis. These projections are directly obtained through the acquisition of the central k-space line only and it can readily be seen that the projection image corresponds well with the location of protons excited along the magnetic iso-surface. It is to be noted that the images of FIGS. 7a and 7b are shown for illustration purpose since they are not required in the present method.

Figure 8A:
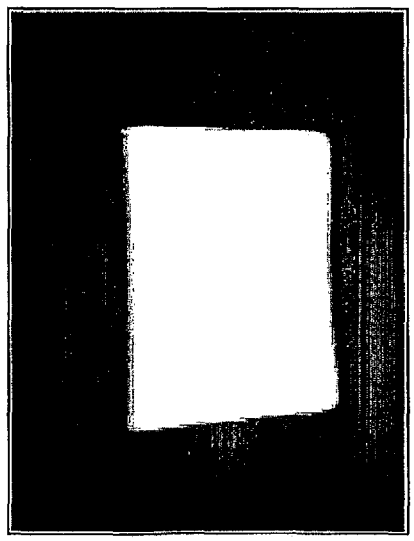
FIGS. 8a through 8d show transversal views of the effects of the RF sync excitation frequency of 500 Hz, 800 Hz, 1000 Hz, and 15000 Hz, respectively in FIGS. 8a, 8b, 8c and 8d, on the MR images.
Figure 8B:
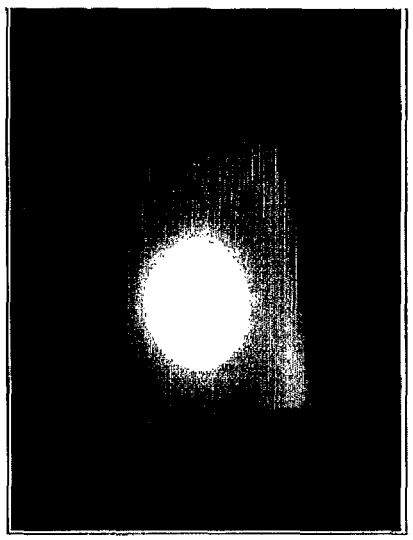
Figure 8D:
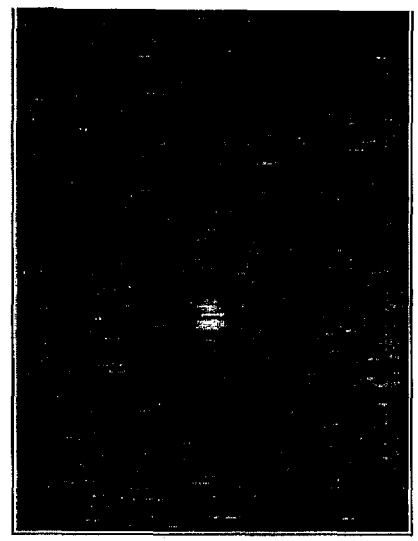
Figure 8C:
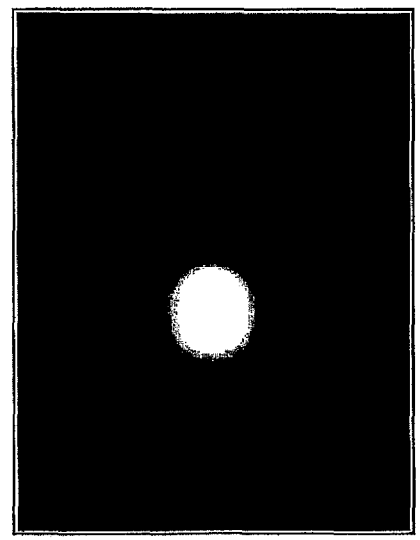

FIGS. 8a through 8d show how the selection of the RF excitation frequency affects the MR images in two antagonistic ways. Increasing the frequency offset ensures that only the induced field of the dipole is responsible for the selective excitation of the spins. However, the Contrast to Noise Ratio (CNR) is decreased. On the other hand, decreasing the offset may excite additional regions of high susceptibility difference such as near air-water interfaces. FIG. 8a shows a homogeneous volume excited with a frequency of 500 Hz and a bandwidth of 1.111 kHz. The non-specific selection is due to the fact that the frequency bandwidth includes the Larmor frequency. When the frequency is increased to 800 Hz, some selectivity is noticeable as depicted in FIG. 8b, although air-water interfaces still degrade the contrast between the marker and the background. On the contrary, FIG. 8c and d show images where the excitation is restricted to a volume surrounding the sphere, although increasing the frequency by a large amount will decrease the CNR as depicted in FIG. 8d.

It is to be noted that it is possible to modify the frequency that excites the object during the tracking since the CNR may vary depending on the homogeneity of the area surrounding the object. For example, at air-tissue interface, the frequency offset must be increased to obtain an adequate CNR.

As mentioned hereinabove, the excitation frequency offset and bandwidth affect the signal, and can be used to adjust the CNR. While a low frequency offset excites a large volume and thus gives a high signal intensity, it may also excites region with high susceptibility difference, such as air-tissue interfaces, and hence causes a reduction of the CNR. On the other hand, a higher frequency increases selectivity and confines the excitation to region surrounding the marker while still decreasing the CNR by a decrease in signal intensity. Given that the CNR is important to optimize when choosing the sequence parameters, it was investigated against the excitation frequency offset for the 1 mm chrome steel sphere. The CNR was also investigated against the sphere diameter (1.5, 1.2, 1.0, 0.8, 0.5, and 0.3 mm) for a fixed RF frequency offset and bandwidth.

Figure 10:
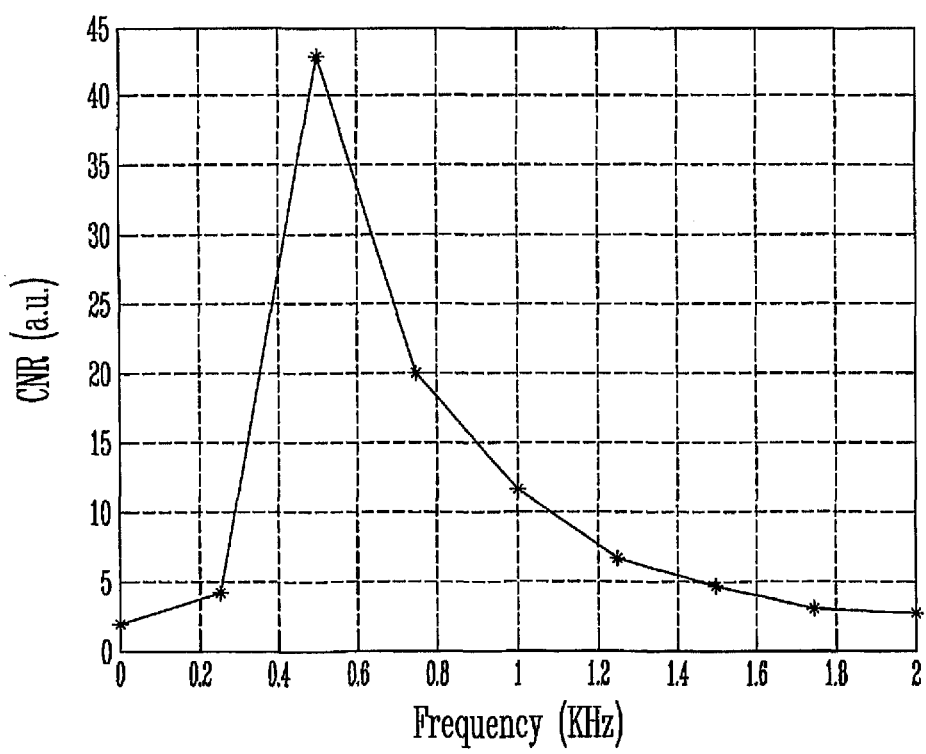
FIG. 10 illustrates the Contrast to Noise Ratio (CNR) versus the frequency for a chrome steel sphere having a 1 mm diameter); the bandwidth being 250 Hz.

FIG. 10 shows the CNR when varying the excitation frequency offset from zero to 2 kHz with successive increments of 250 Hz, at a constant bandwidth of 250 Hz; hence avoiding overlap between successive RF excitations. In this particular situation, the optimal excitation offset frequency in term of CNR was found to be 500 Hz corresponding to a frequency bandwidth extending from 375 to 625 Hz.

Figure 11:
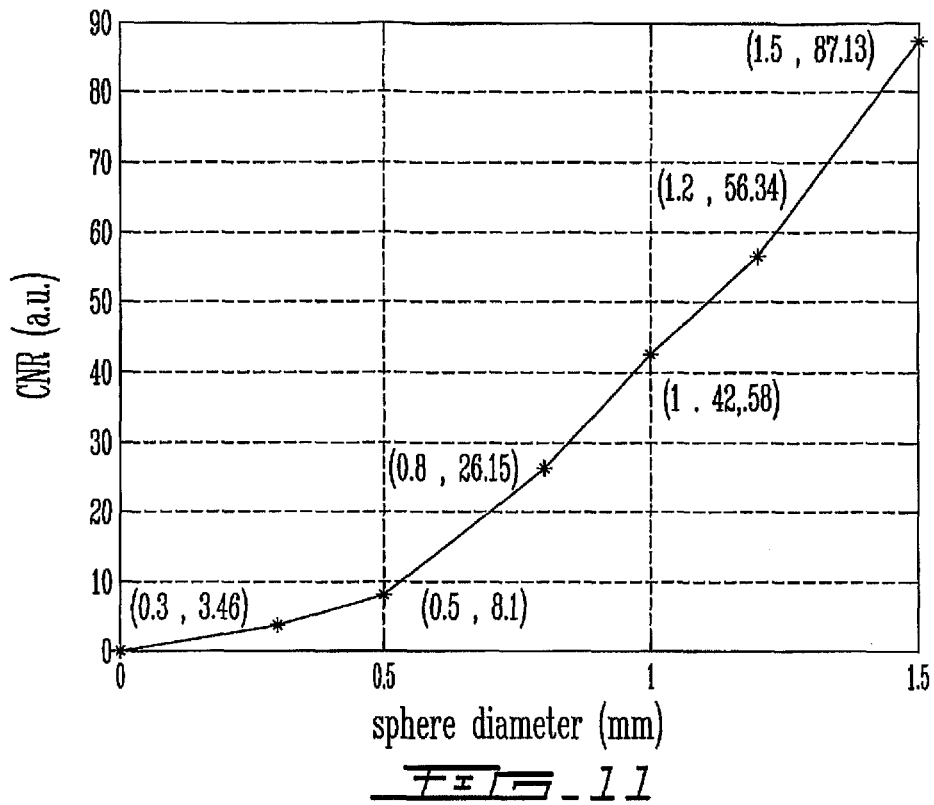
FIG. 11 illustrates the CNR versus the sphere diameter for an RF excitation offset of 800 Hz and a bandwidth of 1 kHz.

FIG. 11 shows the CNR for different sphere diameter obtained with an excitation bandwidth frequency extending from 500 Hz to 1.5 kHz. The CNR exhibits a cubic decrease with smaller sphere diameter as predicted by theory since the dipolar field is function of the cube of the radius of the sphere. A bead diameter of 300 μm can be detected with a CNR of 3.46.

Real time implementation, however, brings new difficulties that can be problematic for tracking. For example, the effect of motion during RF excitation can have an impact on the flip angle experienced by the spins. Furthermore, only some of the excited spins will experience the refocusing pulse. Finally, magnetic inhomogeneities will shift the echo time because the induced magnetic field will not be correctly balanced by the refocusing pulse. In order to quantify these errors, the MRI positioning data was compared with the results obtained by an optical tracking system consisting of a pixelink capture SE camera. The trajectory traveled by the ferromagnetic sphere was filmed and then the TTL output of the Siemens AVANTO MRI system was used to synchronize the sequence with the camera. The spin echo implementation corrects for the dephasing caused by the magnetic field inhomogeneities. The sequence parameters were: TE=9.8 ms, flip angle=90°, frequency offset=1,000 Hz, a refresh rate of 10 projections/second, 1024 sampled points in the read direction, and a FOV in the x direction of 300 mm resulting in a pixel size of 0.293 mm. The ferromagnetic device was mounted on the tip of a catheter and was moved manually. Positions were found by correlating each new projection with the first one acquired, which was considered as the reference. The trajectory given by the camera was obtained by manually sketching the pixel coordinate of the sphere in each frame.

Figure 12:
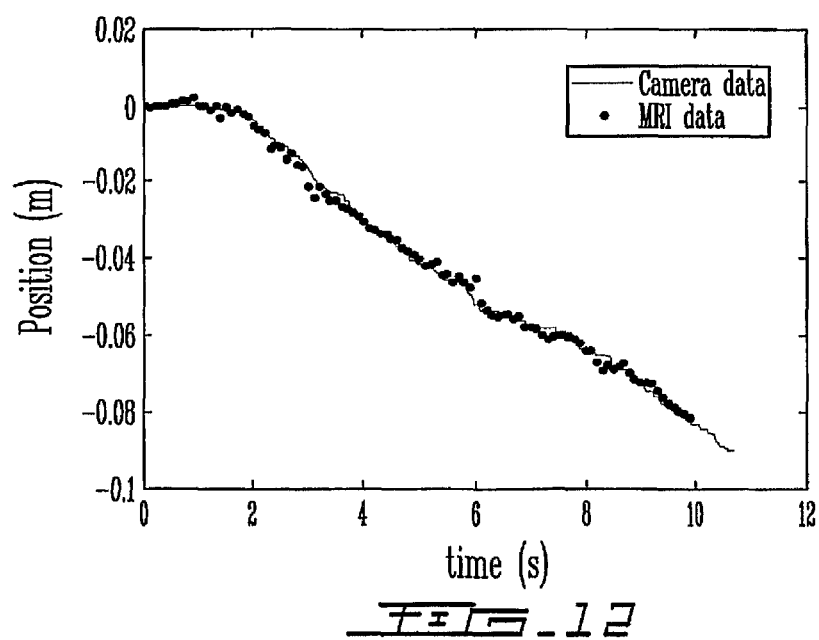
FIG. 12 illustrates the trajectory traveled by the ferromagnetic sphere as given by the camera and the correlation of MRI projections.

Previous results made with a static sphere give an average error of 0.102 mm between the real position and the measured one. In the dynamic case, however, this value is found to be approximately 1.2 mm. This increase in the error is due to the added error from the visual tracking and to the reduced SNR at the short repetition time (TR) used. However this is enough to track the device efficiently, as depicted by FIG. 12, where the trajectories obtained through both MRI projections and optical means are superimposed.

Magnetic Field Mapping

Generally, a field inhomogeneity of even 3.35 ppm, which is the mean chemical shift between fat and water, affects the image quality. If this variation is more important, more severe geometric and intensity distortions may be generated in the reconstructed images. Correction requires knowledge of the magnitude and spatial extent of the magnetic field perturbation. This field map can be obtained either experimentally or theoretically, although, for the latter case, arbitrary geometries prove more difficult since no analytical equation describes the induced magnetic field.

Figure 13:
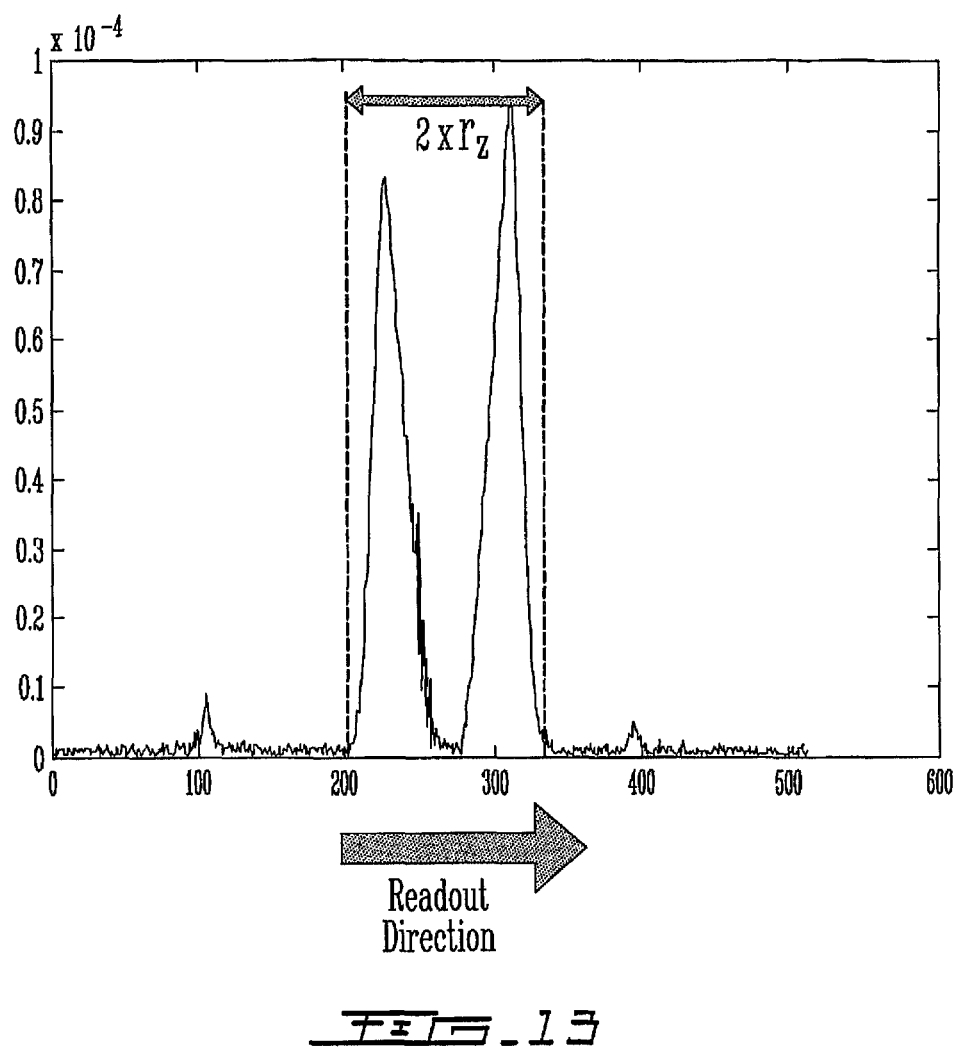
FIG. 13 illustrates a projection along the z-axis used to find the $r_z$ value.

Since the excitation RF frequency and bandwidth are known when using MS-SET, the value of the magnetic field induced from the marker, $B'(0, 0, rz)$, can be deduced. Having the value of the induced magnetic field in a particular location allow us to find the magnetic moment of the magnetic source. This is achieved by inverting Equation 1 considering only the z component of the magnetic field. FIG. 13 show how rz is obtained from a projection. Once the magnetic moment is determined the induced magnetic field from the marker or the objects in any location in space is obtained by solving Equation 1.

Example of Application

It is possible to mount a magnetic-susceptible object on a tethered probe, such as on the tip of a catheter, so as to perform an exploratory, a diagnosis or curative intervention, for example in the vascular system of a subject. In this manner, the tethered probe can be precisely located during the intervention by tracking the magnetic-susceptible object provided on the tip thereof.

An example of a magnetic-susceptible object is a coil made of 30 gauge wire enrolled about 12 times at the ens of a 1.2 mm coaxial cable can be used to induce inhomogeneities in the magnetic field.

Before performing such an intervention, the vascular map of the subject on which the intervention is to be performed must be known. Accordingly, at the beginning of the intervention session, one can use the MRI system to acquire sufficient data to accurately represent the vascular map of the subject in 3D coordinate system. With this map, an intervention can be planned, i.e. the path that the tethered probe must follow from its point of entry to its interventional sites is linked according to the 3D coordinate system.

In brief, the steps described hereinbelow are advantageously followed:

1) acquiring the data describing the 3D vascular map of the subject, according to a 3D coordinate system;
2) planning the intervention by determining the path that the tethered probe must follow, according to the 3D vascular map;
3) tracking, in real time, the 3D position of the magnetic susceptible object; and
4) performing the intervention while superposing the 3D position of the object onto the acquired map to thereby visualize the position of the object in the subject.

Of course, one skilled in the art will understand that the 3D position of the object can be superposed on images taken before or during the intervention.

It is to be understood that the magnetic-susceptible object is tracked in real time, and that the steps described hereinabove are to be repeated at a certain frequency during the intervention. The more accurate is to be the intervention, the greater must be the tracking frequency to allow proper real-time 3D visualisation of the object in the subject. Typically, one can expect a frequency of $10 s^{-1}$ and above.

In the same way, it is possible to track an untethered magnetic-susceptible object. In this case, the object is likely to be a microdevice, small enough to freely move into the blood vessels of the subject, the maximal size of the microdevice depending on the type of blood vessels at which the intervention aims, i.e. arteries, veins, capillaries, as described hereinabove. In this case, the microdevice itself is to be used for an exploratory, a diagnosis or a curative intervention. Such an intervention session also comprises a vascular map acquiring step, a planning step, and the intervention performing step itself.

In the case of an untethered magnetic-susceptible microdevice, the latter can flow passively along with the blood stream, or be actively propelled by using a magnetic resonance propulsion (MRP) technique.

Using the same MRI system for both tracking and propelling such an untethered microdevice avoids additional communication and synchronization latencies between two separate systems. This facilitates the implementation of an overall application within tight real-time constraints. This approach leads to a more robust and effective system because the MR-tracking method and device is time-multiplexed and operated in conjunction with the generation of propulsion gradients.

Figure 14:
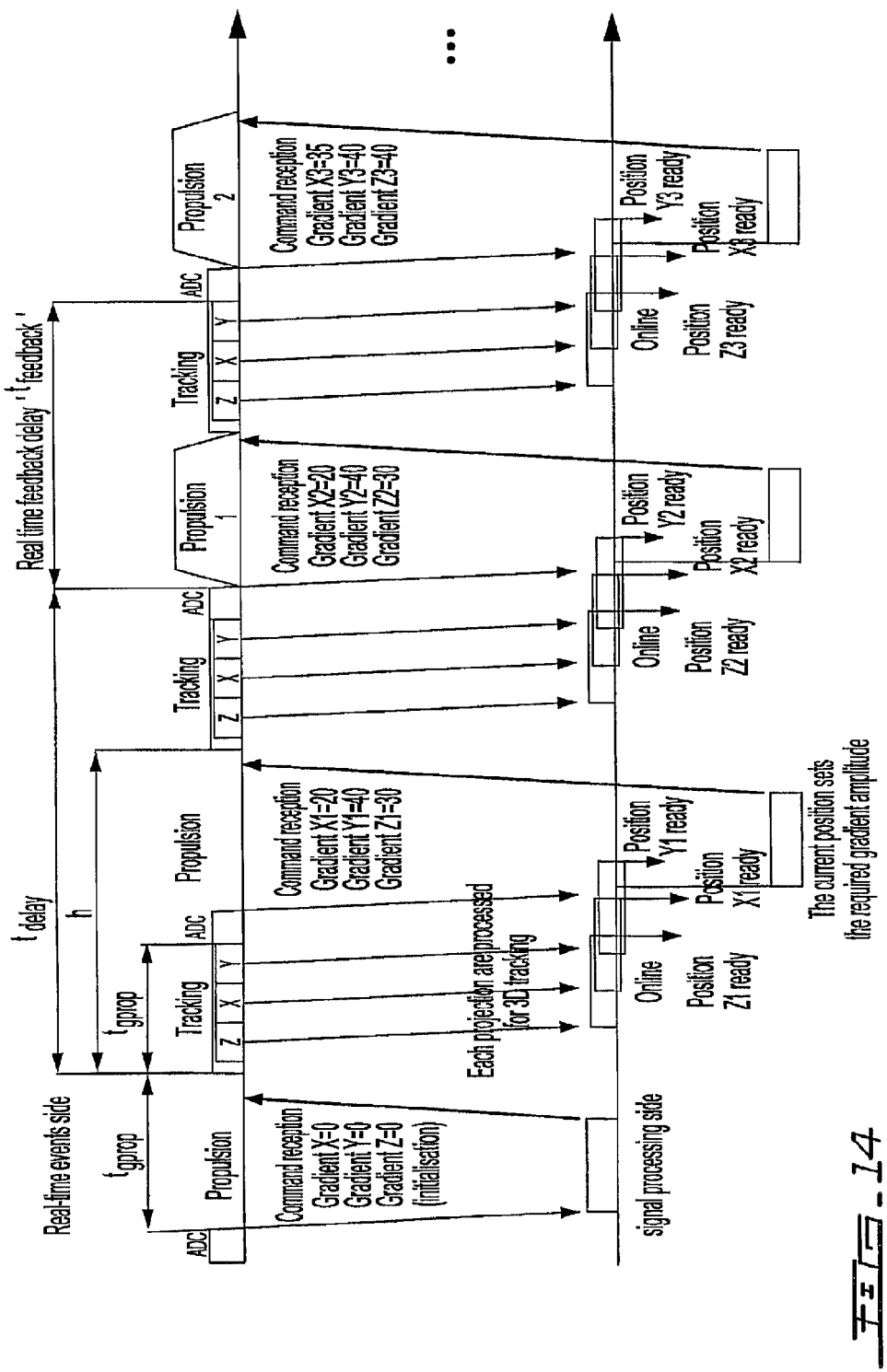
FIG. 14 is a representation of a possible integration of MR-tracking and MRP.

Since most recent MRI systems include real-time capabilities in their architecture, they allow for temporal multiplexing of propulsion and tracking. A possible implementation is shown in FIG. 14. In the Real-time events side gradients and radiofrequency are played out in order to track or to propel the ferromagnetic object. The amplitude of the propulsion gradients is determined according to the current position and the final destination of the object.

Although the present invention has been described hereinabove by way of non-restrictive illustrative embodiments thereof, these embodiments can be modified without departing from the spirit and nature of the subject invention.

What is claimed is:

1. A method for magnetic resonance tracking comprising:
providing a magnetic-susceptible object in an MRI system, wherein said object is magnetically saturated and forms a magnetic dipole;
selecting a predetermined frequency offset corresponding to a desired magnetic iso-surface about the object;
generating the predetermined frequency in the MRI system to selectively excite an induced magnetic iso-surface about the object having a shape corresponding to the magnetic dipole and a size larger than the object;
applying a readout gradient in the MRI system and projecting the excited induced magnetic iso-surface on three axes G1, G2 and G3 in k-space to obtain three projection lines representing the position of the excited induced magnetic iso-surface on the three axes; and
calculating the position of the object from the three projections.

2. A method for magnetic resonance tracking as defined in claim 1, wherein the three axes G1, G2 and G3 are orthogonal.

3. A method for magnetic resonance tracking as defined in claim 1, further comprising mounting the magnetic-susceptible object on a medical instrument.

4. A method for magnetic resonance tracking as defined in claim 1, wherein the magnetic-susceptible object includes a coil, and the method further comprises installing the coil on a medical instrument.

5. A method for magnetic resonance tracking as defined in claim 1, wherein the object includes an untethered microdevice, the method further comprising propelling the untethered microdevice using magnetic resonance propulsion.

6. A method for magnetic resonance tracking as defined in claim 1, further comprising obtaining positions of the object at different times by repeating said selectively exciting, projecting and calculating at a given tracking frequency.

7. A method for magnetic resonance tracking as defined in claim 6, wherein obtaining the positions of the object is performed in real time.

8. A method for magnetic resonance tracking as defined in claim 1, wherein calculating the position of the object comprises applying a correlation function on the three projections on the three axes G1, G2 and G3 of a line in k-space.

9. A method for magnetic resonance tracking as defined in claim 1, wherein calculating the position of the object further includes locating the absolute position of the object on a 3D system of reference.

10. A method for magnetic resonance tracking as defined in claim 1, further comprising storing the position of the object calculated.

11. A method for magnetic resonance tracking as defined in claim 1, further comprising displaying the calculated position of the object.

* * * * *